US00PP27611P3

(12) United States Plant Patent
Geibel

(10) Patent No.: US PP27,611 P3
(45) Date of Patent: Jan. 24, 2017

(54) ***PELARGONIUM* PLANT NAMED 'PACHAFRED'**

(50) Latin Name: *Pelargonium peltatum*
Varietal Denomination: Pachafred

(71) Applicant: Martin Geibel, Dresden (DE)

(72) Inventor: Martin Geibel, Dresden (DE)

(73) Assignee: Elsner pac Jungpflanzen GbR, Dresden (DE)

( * ) Notice: Subject to any disclaimer, the term of this patent is extended or adjusted under 35 U.S.C. 154(b) by 63 days.

(21) Appl. No.: 14/545,190

(22) Filed: Apr. 4, 2015

(65) Prior Publication Data

US 2016/0295779 P1 Oct. 6, 2016

(51) Int. Cl.
*A01H 5/02* (2006.01)

(52) U.S. Cl.
USPC ..... Plt./332

(58) Field of Classification Search
USPC ..... Plt./332
See application file for complete search history.

*Primary Examiner* — Susan McCormick Ewoldt
(74) *Attorney, Agent, or Firm* — C. A. Whealy

(57) ABSTRACT

A new and distinct Ivy Geranium plant named 'Pachafred', characterized by its uniformly mounded and cascading to trailing plant habit; vigorous growth habit; freely basal branching habit; freely flowering habit; and bright red single-type flowers that are positioned above and beyond the foliar plane.

1 Drawing Sheet

Botanical designation: *Pelargonium peltatum.*
Cultivar denomination: 'PACHAFRED'.

BACKGROUND OF THE INVENTION

The present invention relates to a new and distinct cultivar of Ivy Geranium plant, botanically known as *Pelargonium peltatum*, and hereinafter referred to by the cultivar name 'Pachafred'.

The new Ivy Geranium plant is a product of a planned breeding program conducted by the Inventor in Dresden, Germany. The objective of the breeding program is to develop new vigorous Ivy Geranium plants with uniform plant habit and numerous attractive flowers.

The new Ivy Geranium plant originated from a cross-pollination made by the Inventor in Dresden, Germany during the summer of 2009 of two unnamed proprietary selections of *Pelargonium peltatum*, not patented. The new Ivy Geranium plant was discovered and selected by the Inventor as a flowering plant from within the progeny of the stated cross-pollination in a controlled greenhouse environment in Dresden, Germany in June, 2010.

Asexual reproduction of the new Ivy Geranium plant by vegetative terminal cuttings in a controlled greenhouse environment in Dresden, Germany since December, 2010 has shown that the unique features of this new Ivy Geranium plant are stable and reproduced true to type in successive generations.

SUMMARY OF THE INVENTION

Plants of the new Ivy Geranium have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Pachafred'. These characteristics in combination distinguish 'Pachafred' as a new and distinct Ivy Geranium plant:

1. Uniformly mounded and cascading to trailing plant habit.
2. Vigorous growth habit.
3. Freely basal branching habit.
4. Freely flowering habit.
5. Bright red single-type flowers that are positioned above and beyond the foliar plane.

Plants of the new Ivy Geranium differ primarily from plants of the parent selections in plant habit as plants of the new Ivy Geranium are more uniform than plants of the parent selections.

Plants of the new Ivy Geranium can be compared to plants of the *Pelargonium peltatum* 'Pachafdared', disclosed in a U.S. Plant patent application Ser. No. 14/545,186, filed concurrently. In side-by-side comparisons conducted in Dresden, Germany, plants of the new Ivy Geranium differed from plants of 'Pachafdared' in the following characteristics:

1. Plants of the new Ivy Geranium were shorter than plants of 'Pachafdared'.
2. Plants of the new Ivy Geranium had slightly larger flowers than plants of 'Pachafdared'.
3. Flowers of plants of the new Ivy Geranium were lighter red in color than flowers of plants of 'Pachafdared'.

Plants of the new Ivy Geranium can be compared to plants of the *Pelargonium peltatum* 'Pachaforg', disclosed in a U.S. Plant patent application Ser. No. 14/545,188, filed concurrently. In side-by-side comparisons conducted in Dresden, Germany, plants of the new Ivy Geranium differed from plants of 'Pachaforg' in the following characteristics:

1. Plants of the new Ivy Geranium were broader than plants of 'Pachaforg'.
2. Leaves of plants of the new Ivy Geranium were darker green in color than leaves of plants of 'Pachaforg'.

3. Plants of the new Ivy Geranium had larger flower umbels than plants of 'Pachaforg'.
4. Plants of the new Ivy Geranium and 'Pachaforg' differed in flower color as plants of 'Pachaforg' had bright orange-colored flowers.

BRIEF DESCRIPTION OF THE PHOTOGRAPH

The accompanying colored photograph illustrates the overall appearance of the new Ivy Geranium plant showing the colors as true as it is reasonably possible to obtain in colored reproductions of this type. Colors in the photograph may differ slightly from the color values cited in the detailed botanical description which accurately describe the colors of the new Ivy Geranium plant.

The photograph comprises a side perspective view of a typical flowering plant of 'Pachafred' grown in a container.

DETAILED BOTANICAL DESCRIPTION

The aforementioned photograph and following observations, measurements and values describe plants grown in 19-cm containers during the summer in a glass-covered greenhouse in Dresden, Germany and under cultural practices typical of commercial Ivy Geranium production. During the production of the plants, day temperatures averaged 18° C., night temperatures averaged 16° C. and light levels ranged from 15 kilolux to 100 kilolux. Plants were pinched two times and were nine months old when the photograph and the detailed description were taken. In the detailed description, color references are made to The Royal Horticultural Society Colour Chart, 1995 Edition, except where general terms of ordinary dictionary significance are used.

Botanical classification: *Pelargonium peltatum* 'Pachafred'.

Parentage:

*Female, or seed, parent*.—Unnamed proprietary selection of *Pelargonium peltatum*, not patented.

*Male or pollen parent*.—Unnamed proprietary selection of *Pelargonium peltatum*, not patented.

Propagation:

*Type*.—By vegetative terminal cuttings.

*Time to initiate roots, summer*.—About 18 days at temperatures about 20° C.

*Time to initiate roots, winter*.—About 22 days at temperatures about 20° C.

*Time to produce a rooted young plant, summer and winter*.—About four weeks at temperatures about 18° C. to 20° C.

*Root description*.—Fine, fibrous; white in color.

*Rooting habit*.—Freely branching; dense.

Plant description:

*Plant and growth habit*.—Uniformly mounded and cascading to trailing plant habit; broad inverted triangle; densely foliated; vigorous growth habit and rapid growth rate; freely basal branching habit with numerous lateral branches developing per plant.

*Plant height, to top of umbels*.—About 35 cm.

*Plant height, to top of foliar plane*.—About 22 cm.

*Plant width*.—About 70 cm.

*Lateral branches*.—Length: About 70 cm. Diameter: About 4 mm. Internode length: About 4 cm. Texture: Pubescent. Color: Close to 147B.

Leaf description:

*Arrangement*.—Opposite; simple.

*Length*.—About 4 cm.

*Width*.—About 7 cm.

*Shape*.—Palmately lobed.

*Apex*.—Pointed.

*Base*.—Cordate.

*Margin*.—Entire, lobed.

*Venation pattern*.—Palmate.

*Texture, upper surface*.—Pubescent; rough; leathery.

*Texture, lower surface*.—Sparsely pubescent.

*Color*.—Developing and fully expanded leaves, upper surface: Close to 137A; venation, close to 144A. Developing and fully expanded leaves, lower surface: Close to 146A; venation, close to 144A. Zonation pattern: Intensity: Distinct. Location: About 2.5 cm from margin. Width: About 1 cm. Color: Darker than 139A.

*Petioles*.—Length: About 3 cm. Diameter: About 2 mm. Texture, upper and lower surfaces: Pubescent; rough. Color, upper and lower surfaces: Close to 147B.

Flower description:

*Flower arrangement and flowering habit*.—Single-type rotate flowers arranged in roughly hemispherical umbels arising from apical leaf axils; umbels displayed above and beyond the foliar plane on strong flexible peduncles; umbels and flowers face upright to outwardly; freely flowering habit; about six flowers per umbel and about 50 umbels developing per plant.

*Fragrance*.—None detected.

*Flowering season*.—Early flowering habit, plants begin flowering about three months after planting; in the garden in Germany, flowering begins in May and continues until frost in the autumn.

*Flower longevity*.—Flowers last about six to ten days on the plant; umbels last about three to four weeks on the plant; flowers not persistent.

*Umbel height*.—About 5 cm.

*Umbel diameter*.—About 10.5 cm.

*Flower diameter*.—About 5 cm.

*Flower depth (height)*.—About 1 cm.

*Flower buds*.—Length: About 1.1 cm. Diameter: About 5 mm. Shape: Spindle-shaped. Color: Close to 146B.

*Petals*.—Quantity per flower: About five in single whorl; petals somewhat imbricate. Length: About 2.8 cm to 3.2 cm. Width: About 2.4 cm to 2.5 cm. Shape: Obovate. Apex: Rounded. Base: Cuneate. Margin: Entire. Texture, upper and lower surfaces: Smooth, glabrous; velvety. Color: When opening and fully opened, upper surface: Brighter than 45A; towards the base, close to 155D; venation, towards the base, close to 64A; color becoming closer to 45A with development. When opening and fully opened, lower surface: Close to 44C; towards the base, close to 155D; venation, towards the base, close to 64C.

*Petaloids*.—None observed.

*Sepals*.—Quantity per flower: About five arranged in a single whorl. Length: About 1.3 cm. Width: About 3 mm. Shape: Lanceolate. Apex: Acute. Margin: Entire. Texture, upper and lower surfaces: Slightly pubescent. Color, upper surface: Close to 146B. Color, lower surface: Close to 146C.

*Peduncles (umbel stems)*.—Length: About 13 cm. Diameter: About 2 mm. Strength: Strong, flexible. Angle: Upright to outwardly slanted. Texture: Pubescent. Color: Close to 146B.

*Pedicels* (*individual flower stems*).—Length: About 2.8 cm. Diameter: About 1.5 mm. Strength: Strong; flexible. Texture: Pubescent. Color: Close to 146B.

*Reproductive organs*.—Androecium: Stamen quantity per flower: About eight. Anther length: About 2 mm. Anther shape: Tubular. Anther color: Darker than 79A. Pollen amount: Moderate. Pollen color: Close to 167A. Gynoecium: Pistil quantity per flower: One. Pistil length: About 3 mm. Stigma shape: Five-parted. Stigma color: Close to 187A. Style length: About 1 mm. Style color: Close to 11D. Ovary color: Close to 138D. Seeds and fruits: Seed and fruit development have not been observed on plants of the new Ivy Geranium.

Disease & pest resistance: Plants of the new Ivy Geranium have not been observed to be resistant to pathogens and pests common to Ivy Geranium plants.

Temperature tolerance: Plants of the new Ivy Geranium have been observed to tolerate temperatures ranging from about 1° C. to about 35° C. to 40° C.

It is claimed:

1. A new and distinct Ivy Geranium plant named 'Pachafred' as illustrated and described.

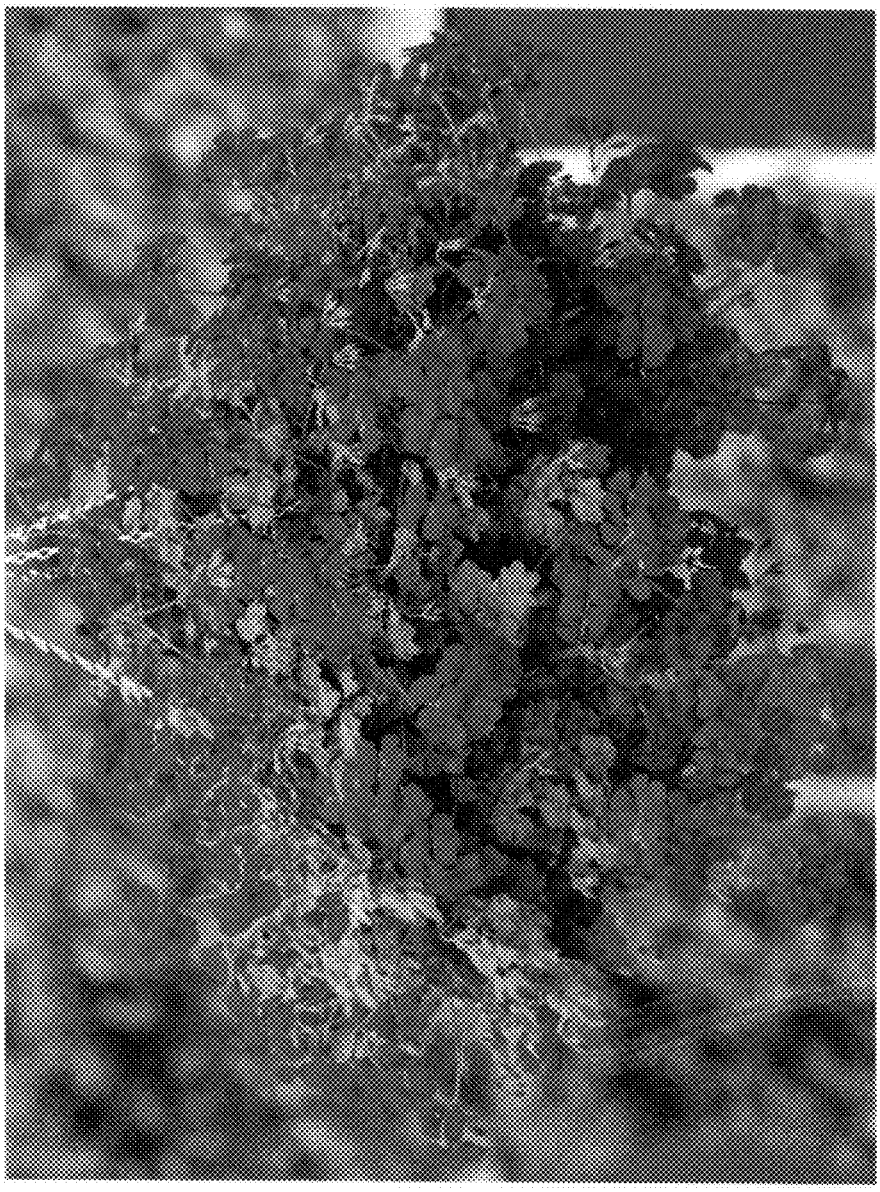

* * * * *